United States Patent [19]

Brandon

[11] 4,315,426
[45] Feb. 16, 1982

[54] FRICTION COEFFICIENT MEASUREMENT FROM A MOVING VEHICLE

[76] Inventor: Ronald E. Brandon, 1734 Lenox Rd., Schenectady, N.Y. 14611

[21] Appl. No.: 110,985

[22] Filed: Jan. 10, 1980

[51] Int. Cl.³ .......................................... G01N 19/02
[52] U.S. Cl. ........................................ 73/9; 73/146; 73/862.04
[58] Field of Search ..................... 73/9, 133 R, 146; 340/665, 52 R, 40, 580

[56] References Cited
U.S. PATENT DOCUMENTS 4,098,111  7/1978  Hardmark et al. .................. 73/9
4,212,063  7/1980  Hardmark ............................ 73/9

Primary Examiner—Charles A. Ruehl
Assistant Examiner—Denis E. Corr

[57] ABSTRACT

Apparatus and methods are disclosed for detecting slippery road conditions directly from a moving vehicle. A special probe is momentarily lowered to the road surface from the moving vehicle. A coefficient of friction is determined by ratio of the verticle and friction forces. A display provides the operator with a proper indication of roadway conditions.

3 Claims, 5 Drawing Figures

FRICTION COEFFICIENT MEASUREMENT FROM A MOVING VEHICLE

This invention relates to detection system and more particularly to systems for detecting slippery conditions on the surface of highways.

A frequent cold-weather road hazzard is the possibility of ice which, if present, requires great care from the operator of the vehicle. Unfortunately such ice may be difficult to detect by visual means and further may vary significantly with small changes of altitude or location such that operators of vehicles have great difficulty knowing how slippery the roadbed may be. Thus imprudent speed may unknowingly be used on dangerously slippery roads. Conversely, unnecessary low speed and care may be used on roads where the conditions are actually quite safe.

A number of systems have been proposed for detecting wet and icy conditions on a surface but each has one or more serious shortcomings. Such systems can be categorized as indirect or direct. Indirect systems do not monitor the actual surface condition but instead attempt to predict the surface conditions by measuring air temperature and humidity. Needless to say, they are not reliable because ambient temperature and humidity are not consistently accurate indicators of the presence or absence of ice on an exposed surface. Some of the direct measurement systems, such as those requiring microwave or beta radiation, are quite expensive and are not wholly reliable.

A serious drawback of these prior art systems is their dependence on individual static sensors located within a roadway system. To cover the varying conditions of a complicated road network would require excessive numbers of detectors with accompanying problems of cost, maintenance and monitoring. In addition, and perhaps more serious, is the difficulty of interpreting the signals.

It should be recognized that even under conditions known to include ice, snow or rain, that wide ranges of friction capability should be expected that cannot be accurately determined by devices of the prior art.

Still a further difficulty is the lack of information for the operators of vehicles during the lengthy time period required for action by service crews after icing conditions are recognized.

It should likewise be recognized that slippery conditions can occur on oily roads lightly wetted by a rain shower that cannot be properly identified by existing conditions.

Operators of vehicles need direct, accurate information that is not currently available.

The foregoing disadvantages and others of prior systems for detecting slippery road conditions are advantageously overcome in accordance with the present invention.

In this respect, the present invention in its broadest sense applies to moving vehicles depending on friction between vehicle and roadway for their safe and effective operation. It provides such moving vehicles with a measuring system for determining the coefficient of friction for the roadway on which they are traveling. This is accomplished as described below.

Briefly a system is provided so that the operator of a moving vehicle can initiate a sequence of events that:
1. Lowers a probe to the roadbed with the vehicle moving at a predetermined speed.
2. Measures the vertical force to which it is applied to the roadbed.
3. Measures the friction force caused by its full sliding on the roadbed with the rate of slip equal to the vehicle speed.
4. Calculates a coefficient of friction by comparing the friction force and the vertical force.
5. Raises the probe to its normal stored position.
6. Displays friction coefficient to the vehicle operator.
7. Identifies specially slippery conditions.

The above system depends on the physical character of sliding friction coefficients that have been found to be relatively independent of contact force.

In accordance with the foregoing, an outstanding object of the present invention is the improvement of safety for vehicles traveling on potentially slippery roads by providing near to instant, local evaluations of the roadway coefficient of friction.

Another object is to provide evaluation of road surfaces without requiring vehicles to stop, apply brakes or make other potentially dangerous testing maneuvers.

Yet another object is to provide reliable, accurate local evaluations that may be quickly transmitted to road crews and other vehicles.

Still another object is to provide a friction coefficient measuring system that can be calibrated under known roadway conditions to provide highest confidence of accuracy for unknown conditions.

The foregoing and other objects of the present invention will in part be obvious and in part more fully pointed out hereinafter in conjunction with the description of the accompanying in which.

Figure 1:
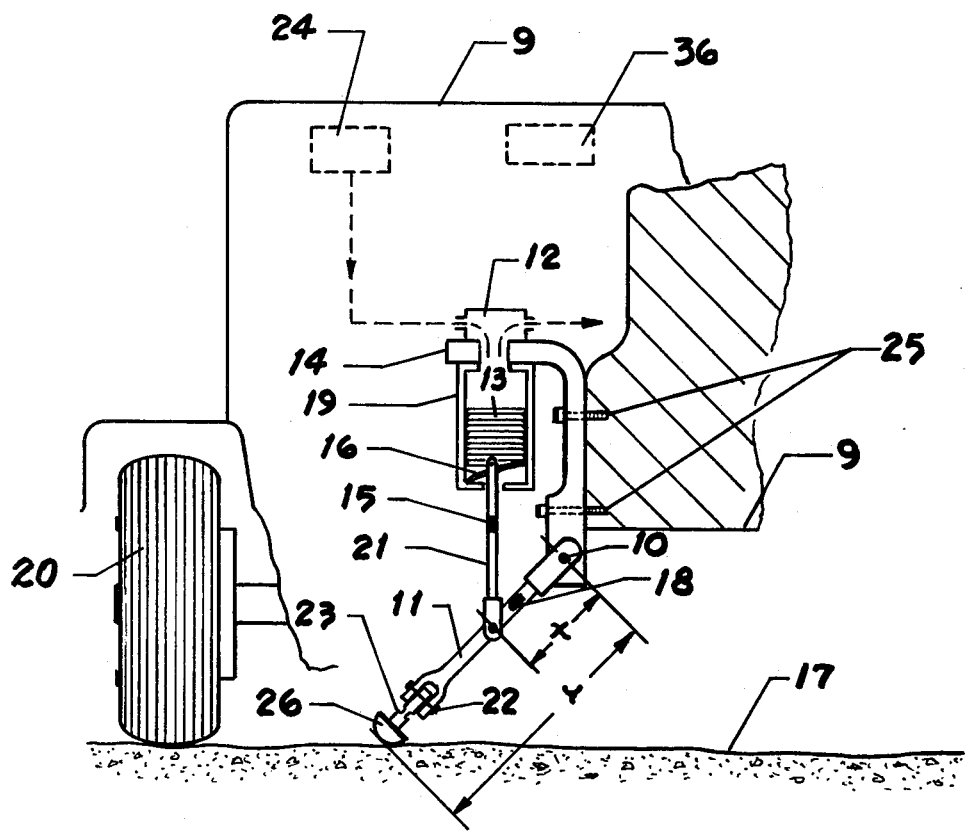
FIG. 1 illustrates a frontal view of a hinged probe system mounted on the lower structure of a moving vehicle in accordance with the present invention.
Figure 2:
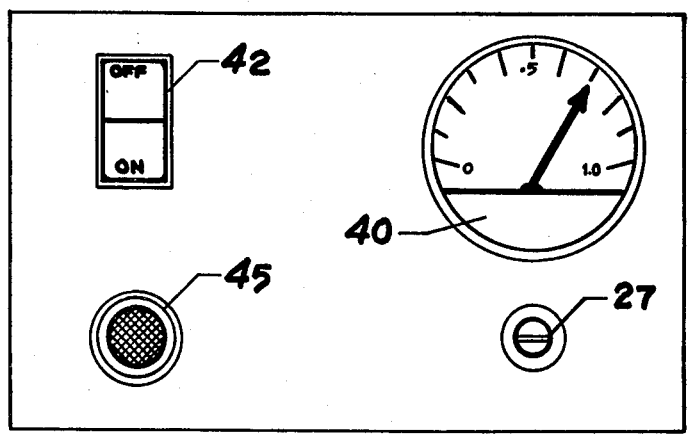
FIG. 2 illustrates an operator's panel arranged in accordance with the present invention.

Referring now to the drawings in greater detail wherein the showings are for the purpose of illustrating a preferred embodiment of the invention and not for the purpose of limiting the same, FIGS. 1-4 illustrate arrangements by which the present invention can be employed to measure and identify the friction coefficient of road surfaces from a moving vehicle.

In this respect my invention is illustrated as being incorporated with a vehicle which can provide a source of electrical power 36, and pressurized air 24. The vehicle 9, is illustrated with wheels 20, operating on a highway whose surface 17, provides a level of friction in cooperation with the wheels 20.

A mounting bracket 14, is shown bolted 25, to the vehicle. At one end of the bracket is a hinge 10, which is oriented to permit vertical motion of a connected probe 11, but to resist probe motion either forward or backward with relationship to the motion of the vehicle 9. At the other end of the bracket 14, an air cylinder 19, is firmly mounted. A pneumatic solenoid valve 12, is mounted on the air cylinder 19, with connection to the vehicle compressed air supply 24. Upon electrical signal the pneumatic solenoid valve 12, is opened to admit air to the air cylinder with the exhaust port closed. At the end of the measurement sequence the solenoid is repositioned to close the air inlet and open the exhaust port.

Entry of air into the air cylinder 19, causes the air piston 13, to move downward, compressing spring 16, and forcing the probe 11, downward and into contact with the road surface, 17. Upon repositioning the solenoid valve 12, the connection to vehicle air supply 24, is closed and the air within the air cylinder is permitted to exhaust. The compressed spring 16, is free to raise the probe 11, to its upper stored position.

Figure 3:
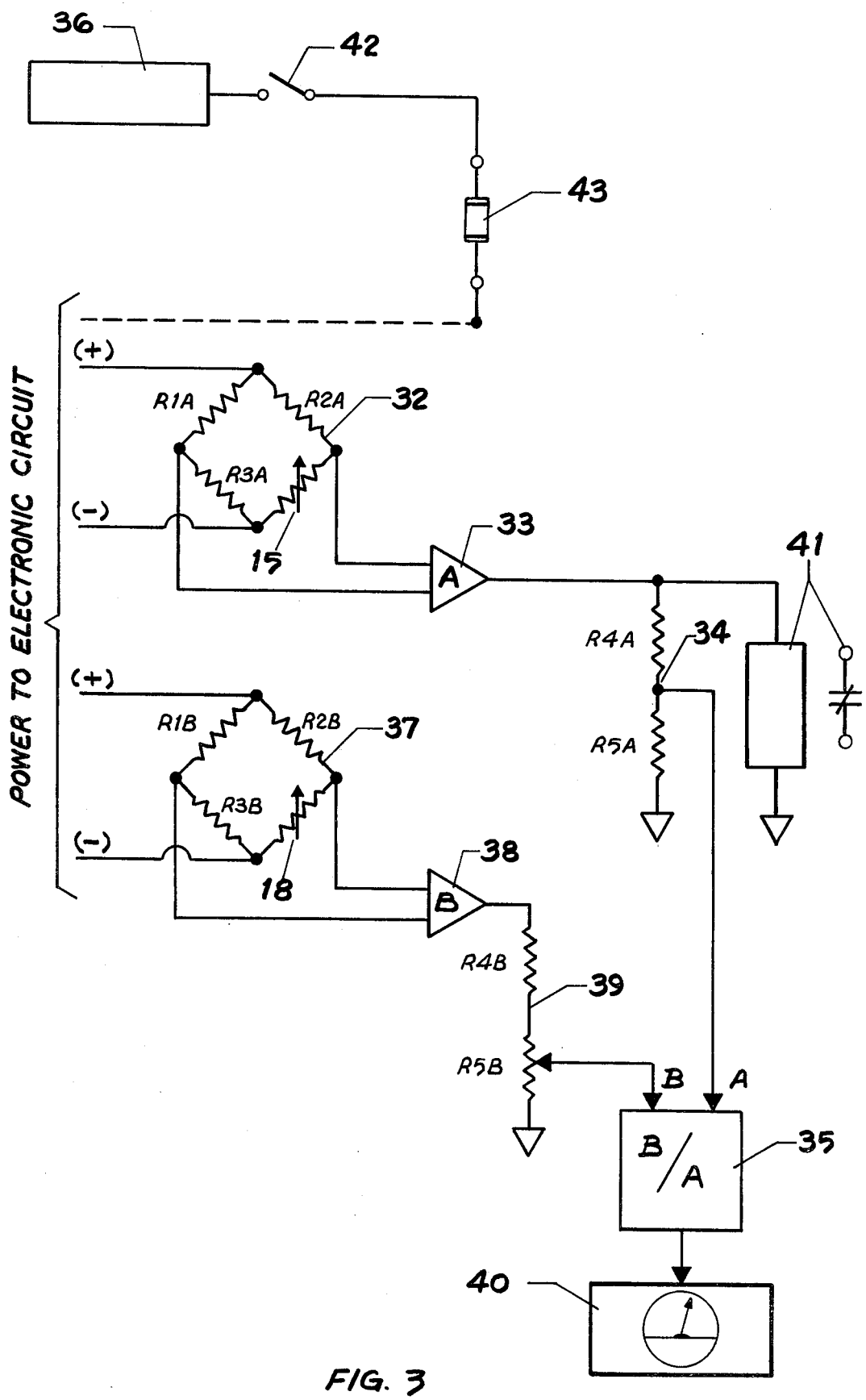
FIG. 3 is a simplified electrical schematic drawing of the sensing and metering circuits used in the invention.

Referring to FIG. 3, the electronic sensing and metering circuit utilized as a part of the invention is indicated as having strain gage inputs 15 and 18, from the piston rod 21, and the leading edge of the probe 11. Strain gage input 15, changes in electrical resistance in proportion to the vertical force exerted by the road sensing probe on the road surface. The resistance changes of strain gage input 15, are detected by the resistance bridge circuit 32, and a voltage is produced and is amplified by 33. Amplifier 33, is of conventional design and has a first order lag characteristic with the 3 db voltage gain point located at 3 Hz in order to filter unwanted electrical noise resulting from surface irregularities. The amplifier output is divided by the resistor pair 34, for input levels appropriate to the divider module 35.

Similarly the probe strain gage input 18, changes in electrical resistance in proportion to the friction force exerted on the road sensing probe by the road surface. The resistance changes of strain gage input 18, are detected by the resistance bridge circuit 37, and a voltage is produced and is amplified by 38. Amplifier 38, is of conventional design and has a first order lag characteristic with the 3 db voltage gain point located at 3 Hz in order to filter unwanted electrical noise resulting from surface irregularities. The amplifier output is divided by the resistor pair 39, for input levels appropriate to the divider module 35. The resistor pair 39, allows for minor adjustment of the signal going to 35. The voltage at input B of divider 35, representing friction force is divided by the voltage at input A of divider 35, representing contact force. This results in an output voltage to meter 40, which is proportional to the road surface coefficient of friction.

A sensing relay 41, detects the voltage output from amplifier 33, and opens relay contact 41, when the amplifier output voltage, representing probe contact force with the road reaches a predetermined level. The use of the relay 41, contact is discussed with reference to FIG. 4. The power for the sensing and metering circuits is applied from the vehicle power source 36, through an on/off switch 42, and a fuse 43.

Figure 4:
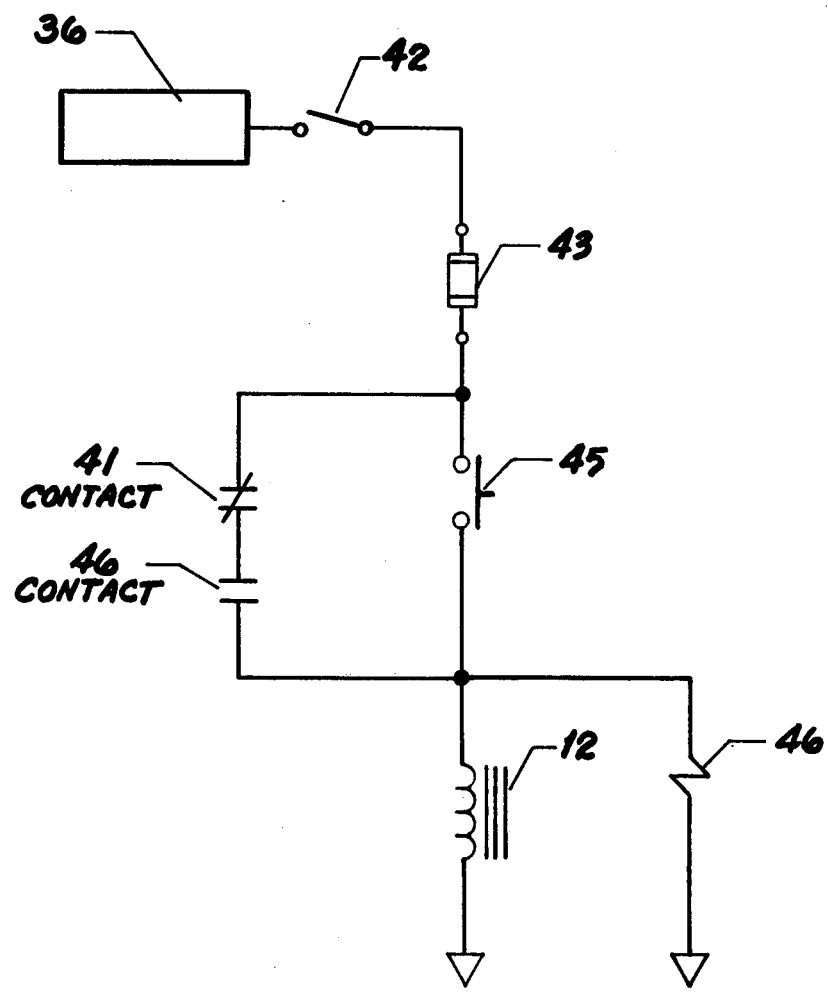
FIG. 4 is a simplified electrical schematic of the probe actuation circuit.
Figure 5:
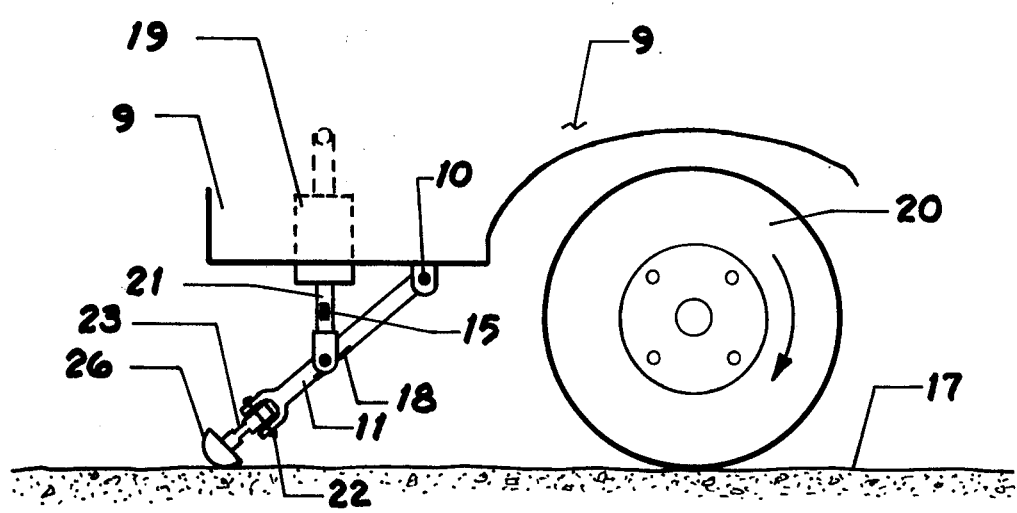
FIG. 5 is a schematic side view of a hinged probe system mounted on the lower structure of a moving vehicle in accordance with the present invention, where the probe is arranged with a backward tilt or curvature while in contact with the roadway.

Referring to FIG. 4, the probe actuation electrical circuit utilized as a part of the invention is indicated as using the same on/off switch 42, and fuse 43, as the sensing circuit. A momentary pushbutton switch 45, is depressed by the operator to initiate a measurement sequence. This will actuate the probe pneumatic solenoid valve 12, which causes the air piston to drive the probe towards the road surface. A relay 46, is picked up at this time which continues power around pushbutton switch 45, through the relay 41 and 46, contacts. Air pressure continues to build in the piston until the probe contact with the road is sufficient to cause the relay 41, contacts to open. When the relay 41, contacts open, the power is removed from the probe pneumatic solenoid valve 12, and air pressure is relieved from the piston and the probe is retracted to the normal stored position.

On FIG. 1 the probe tip 26, is attached to the probe 11, with a breakaway provision and is non rotatable. The probe tip 26, is shown pinned to the probe 11, at 22, with a grooved pin 23, designed to breakaway so as to prevent damage to the remainder of the system should a solid roadway obstruction be encountered.

The probe tip 26, itself is designed with a rounded tip so as to provide a consistent profile to the roadway surface in spite of varying angles of contact.

The probe system should be mounted to track near the same lateral plane of the wheels so as to best represent the friction condition of the road where the tires run. The hinge, wires, and strain gages should be protected by a location selected to minimize damage from wheel-thrown objects, water and ice. A flexible protective cover is suggested to eliminate grime, fluids, and chemicals from sensitive parts. A hinged cover should be used to enclose the moving parts when in the stored position.

It should be stated that friction factor is influenced by the facing materials, their relative velocity, roughness, and the presence of liquids or ice. For best purposes of vehicle operators, the measurement should provide a comparison of existing conditions with those best understood, that is, dry and clean highways. For such conditions, a sliding coefficient of friction can be approximated as 0.7. This would represent a factor proportional to the correcting force that can be applied once a sliding condition has occurred.

Friction Coef. = (Friction force/Vertical force)

The measured friction coefficient is displayed on the meter 40. For dangerously low coefficients an alarm could be actuated such as a buzzer or a red light. Since the actual measurement is momentary, the meter 40, is selected to hold the measured result for a longer time period.

The system can be recalibrated when the vehicle is operating under conditions of known friction coefficients.

A screwdriver adjustment 27, is included with the meter to adjust indications to correct readings for known test conditions. It should be noted that at zero speed, a test reading should be zero, while at conditions of dry, clean macadam roads, the reading should be approximately 0.7. Note also that the 0.7 is correct for rubber tires, not steel probes. This selection is suggested as the most valuable for the operator.

It will be recognized by those familiar with strain gages that the vertical force is a function of the piston rod cross sectional area, the piston rod modulus of elasticity, the ratio of the moment arms X and Y, and the strain gage characteristics of resistance versus strain.

The friction force is determined by strain gage 18, which is mounted on the leading edge of the probe. Sliding friction with the road causes a slight tendency for bending the probe toward the rear which increases tension in the leading edge. This small deflection also stretches the strain gage 18, and increases its electrical resistance as measured by the electronic bridge. The force is a function of the probe length, the location of the strain gage 18, the probe moment of inertia, the probe modulus of elasticity and the characteristics of the strain gage 18. Note that the vertical force caused by the piston does not effect the tension in the leading edge of the probe.

It should be recognized that either current or voltage means can be used to achieve the various signals and that miniaturized components for the bridges, amplifiers, switches and ratioer can be effectively utilized.

It should be further realized that the probe actuator can be operated by hydraulic, vacuum, electrical or air pressure means. The same actuator can be double acting instead of using a spring return.

The probe 11, itself can be advantageously tilted or curved toward the rear of the vehicle to minimize any tendency to chatter as it slides over the road surface.

This geometry, would require minor correction to the calculation of forces used to determine the friction coefficient. The correction required is to eliminate from the friction force the component of bending stress caused in the probe by the vertical force of the piston rod. Since the force is measured and the moment arm known, this can be easily accomplished.

It should be noted also that the vehicle vacuum system could be alternatively used to position the probe instead of compressed air. Likewise, the probe could be manually manipulated by the operator using a lever and cable system.

While what has been described is the preferred embodiment of the invention, other modifications will occur to those skilled in the art and it is, of course, desired to cover in the appended claims all such modification as fall within the true spirit and scope of the invention.

What I claim as new and desire to obtain by Letters Patent of the United States is:

1. A method of measuring and indicating sliding coefficient of friction values for vehicles operating on roadways comprising the steps of:

Lowering an instrumented probe with a non rotatable tip from a vehicle moving with a predetermined speed to momentarily contact the roadway with the non-rotatable tip of said probe in a fully sliding manner with a rate of slip substantially equal to said speed, measuring the vertical and horizontaly loads acting on said probe by means of strain gauges, combining said loads in an electronic unit to produce a signal indicating the sliding coefficient of friction, and producing a display of said coefficient of friction.

2. A method of measuring and indicating as in claim 1 wherein the vertical load determined by the electronic unit is monitored to provide a second signal when a predetermined level has been reached, said second signal being used to trigger automatically the return of the probe to an inactive position.

3. A method of measuring and indicating as in claim 1 wherein the electronic unit includes calculation logic to correct the horizontal force calculation for vertical force components resulting from the use of an instrumented probe which contacts the roadway while including an angle of tilt toward the rear of the vehicle.

* * * * *